(12) United States Patent
Mawhinney

(10) Patent No.: US 6,230,060 B1
(45) Date of Patent: May 8, 2001

(54) SINGLE INTEGRATED STRUCTURAL UNIT FOR CATHETER INCORPORATING A MICROWAVE ANTENNA

(76) Inventor: Daniel D. Mawhinney, 12 Elmwood Dr., Livingston, NJ (US) 07039

( * ) Notice: Subject to any disclaimer, the term of this patent is extended or adjusted under 35 U.S.C. 154(b) by 0 days.

(21) Appl. No.: 09/422,181

(22) Filed: Oct. 22, 1999

(51) Int. Cl.$^7$ ..................................................... A61B 18/18
(52) U.S. Cl. ............................ 607/101; 607/156; 606/33
(58) Field of Search ....................... 607/96, 98, 101–102, 607/154, 156; 606/33

(56) References Cited

U.S. PATENT DOCUMENTS

| | | | | |
|---|---|---|---|---|
| 5,496,271 | * | 3/1996 | Burton et al. | 604/54 |
| 5,509,929 | * | 4/1996 | Hascoet et al. | 607/101 |
| 5,861,021 | * | 1/1999 | Thome et al. | 607/101 |
| 5,928,145 | * | 7/1999 | Ocali et al. | 600/410 |
| 5,987,360 | * | 11/1999 | McGrath et al. | 607/101 |

\* cited by examiner

*Primary Examiner*—Lee Cohen
*Assistant Examiner*—Roy Gibson
(74) *Attorney, Agent, or Firm*—George J. Seligsohn

(57) ABSTRACT

The catheter constitutes a single integrated structural unit comprising a first tubular balloon-supporting structure having a given outer diameter and a second structure inserted therein comprising an antenna and a coaxial cable for energizing the antenna. This permits both the antenna and the longitudinal cable to be wider, without any increase in the given outer diameter, than would be the case if the catheter were a prior-art non-integrated structure in which the tubular first structure and the second structure are separate detached units and, therefore, require clearance therebetween to permit insertion. In both basic and preferred embodiments, the single integrated structural is achieved by an electrically conductive shield attached by spacers to an outer conductor of the coaxial cable. In the basic embodiment, the shield is spaced from both the outer cable conductor and first structure to form inner and outer channels for exiting and entering the circulating balloon-inflating liquid. In the preferred embodiment, the shield is bonded to the inner surface of the first structure to form the entering channel, while the exiting channel is formed by the interior of a tubular inner cable conductor which may also house a thin tube for air inflating a Foley balloon. The inner channels of both embodiments include a ¼ wavelength choke structure at the distal end of the coaxial cable. A modification divides the circumference of the channels into separate angular sectors for independently circulating inflating liquid to any of a plural number of differently-sized balloons.

18 Claims, 7 Drawing Sheets

PRIOR ART

SINGLE INTEGRATED STRUCTURAL UNIT FOR CATHETER INCORPORATING A MICROWAVE ANTENNA

BACKGROUND

1. Field of the Invention

This invention relates to a catheter incorporating a microwave antenna that has an integrated structure and, more particularly, to a urethral balloon catheters having an integrated structure.

2. Description of the Prior Art

Urethra balloon catheters incorporating a microwave antenna for treating prostate disease are known in the art. In this regard, incorporated by reference herein is the teaching of U.S. Pat. No. 5,007,437, which issued Apr. 16, 1991 to Fred Sterzer and is assigned to the same assignee as the present application.

At the present time, microwave balloon treatment of Benign Prostate Hyperplasia (BPH) or prostate cancer involves the use of a urethral catheter with an inflatable balloon to stretch the opening in the enlarged prostate and a radiating antenna to apply microwave energy to the stretched prostatic urethra with the objective of forming a long-lasting biological stent to relieve the symptoms of the affliction. The use of a separate antenna or applicator which must be inserted into the catheter forces several design compromises on both the catheter and the antenna. For both elements to be completely independent and separable, the inserted member, the antenna, must be smaller in diameter than it should be for optimum radiation efficiency and minimum dissipative loss, and the catheter must be larger than needed and provide additional complex flow paths for inflation liquids and/or gasses.

When properly positioned for treatment, the antenna is located near the distal end of the catheter inside the enlarged prostate. It may be in the form of a helical radiator, a capacitive gap, or folded dipole, or other design consistent with the size restrictions (e.g., the length should be no longer than the prostate and the diameter must fit within the restrictive inner diameter of the central lumen of the catheter). For proper impedance match, compactness, and shielding, the connection or feed-line for this antenna must be a coaxial cable consisting of a metal central conducting wire and an outer thin-wall metal cylinder shield with a continuous dielectric insulation between the two metal members.

The catheter must be of a material that is sanitary, sterile, flexible, capable of being extruded with a number of small internal lumens, and tolerant of adhesives used to attach expansion and locating balloons of different physical properties. A number of modern day plastics, e.g. silicones, PET, Teflon®, and Tefzel® are typically used because they are consistent with these requirements. Coincidentally, some of these very same plastics are used for the dielectric insulator in the coaxial feed-line and in some of the antennas.

Thus, the maximum size of the outer diameter of a urethral balloon catheter, with a deflated folded balloon, is limited to a size that will fit into the narrowed urethra of a male patient suffering from a prostate disease. The structure of a prior-art urethral balloon catheter incorporating a microwave antenna comprises separate first and second sub-structures. The first sub-structure consists of the longitudinal body of the prior-art catheter to which the catheter's balloon material is attached. The second part consists of a microwave antenna to which a coaxial cable is attached for supplying microwave power to the antenna. The longitudinal body of the first part includes a centrally-located lumen through which the microwave antenna and coaxial cable of the separate second part can be inserted. This necessitates that the centrally-located lumen diameter be enough larger than the consequent limited diameter of the coaxial cable and the width of the microwave antenna to provide sufficient clearance for their insertion into the centrally-located lumen. The amount of microwave power loss caused by this consequent limited diameter of the coaxial cable and the radiating inefficiency caused by this consequent limited width of the microwave antenna are both undesirable.

Therefore, there is a need for a urethral balloon catheter structure in which the microwave antenna with its attached coaxial cable are integrated with and, therefore, form a permanent part of the longitudinal body of the urethral balloon catheter, since this would permit a desirable increase in the diameter of the coaxial cable and width of the microwave antenna without any increase in the maximum size of the outer diameter of a urethral balloon catheter.

SUMMARY OF THE INVENTION

Broadly, the present invention is directed to an improvement in any catheter incorporating an antenna, wherein the catheter comprises (1) a tubular catheter first structure longitudinally extending from a proximate end thereof to a distal end thereof and (2) a second structure inserted within the tubular catheter first structure that comprises the antenna situated toward the distal end of the tubular catheter first structure and a longitudinal cable that extends from the proximate end of the tubular catheter first structure to the antenna for use in energizing the antenna. In accordance with this improvement, the tubular catheter first structure and the second structure are constructed to comprise a single integrated structural unit.

More specifically, the present invention is directed to an improvement in a urethral balloon catheter incorporating an antenna suitable for use in therapeutically heating a diseased prostate of a male patient with energy radiated from said antenna, wherein the tubular catheter first structure includes an attached inflatable balloon situated near the distal end thereof together with input and output channels for use in circulating a balloon-inflating fluid. The tubular catheter first structure has a given outer diameter sufficiently small to permit it to be inserted inside of the urethra of the male patient with the balloon in its deflated state. The single integrated structural unit permits both the antenna and the longitudinal cable to be wider, without any increase in the given outer diameter, than would be the case if the urethral balloon catheter were a prior-art non-integrated structure in which the tubular catheter first structure and the second structure are separate units that are detached from one another and, therefore, would require clearance between the second structure and the tubular catheter first structure sufficient for a non-permanent insertion of the second structure within the tubular catheter first structure.

DESCRIPTION OF THE PREFERRED EMBODIMENTS

Figure 1A:
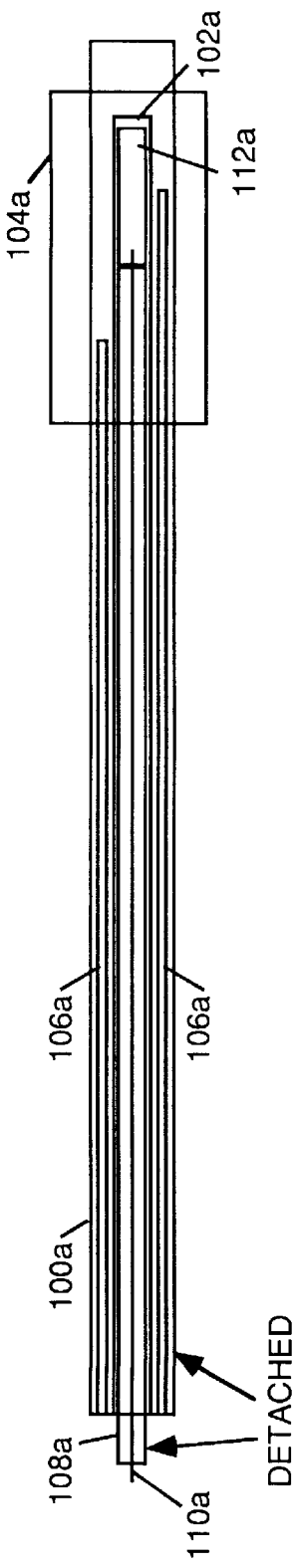
FIGS. 1a and 1b, respectively, are comparative schematic side views of the primary structures of a prior-art urethral balloon catheter incorporating a microwave antenna and such a urethral balloon catheter comprising an integrated structure in accordance with the principles of the present invention.

As schematically shown in FIG. 1a, the primary structure of a prior-art urethral balloon catheter incorporating a microwave antenna comprises first and second detached substructures.

The first detached sub-structure consists of a relatively thick-walled plastic catheter structure 100a having (1) a given outer diameter sufficiently small in size as to be insertable into the urethra of a male patient suffering from a prostate disease and (2) a centrally-located longitudinal lumen 102a extending from the input left end of catheter structure 100a to close to the right end thereof. An inflatable balloon 104a is attached to catheter structure 100a toward the right end thereof. The walls of catheter structure 100a incorporate at least two lumens 106a therethrough for use in continuously circulating a fluid (normally a liquid) under suitable back pressure for inflating the balloon and also for cooling purposes, as known in the art.

The second detached sub-structure, which is insertable within centrally-located lumen 102a of the first attached structure, consists of coaxial cable 108a that comprises an inner conductor 110a having microwave antenna 112a attached to the right end thereof. Microwave antenna 112a may be in the form of a helical radiator, a capacitive gap, or folded dipole, or other design consistent with the size restrictions (e.g., the length should be no longer than the prostate and the diameter must fit within the restrictive inner diameter of the central lumen of the catheter). However, it is necessary that the diameter of centrally-located lumen 102a be sufficiently larger than the outer diameter of coaxial cable 108a and the width of microwave antenna 112a to provide proper clearance for their insertion into centrally-located lumen 102a. This undesirably limits the maximum size of both the outer diameter of coaxial cable 108a and the width of microwave antenna 112a, with its consequent relatively large microwave power loss in coaxial cable 108a and decreased radiating efficiency of microwave antenna 112a.

Figure 1B:
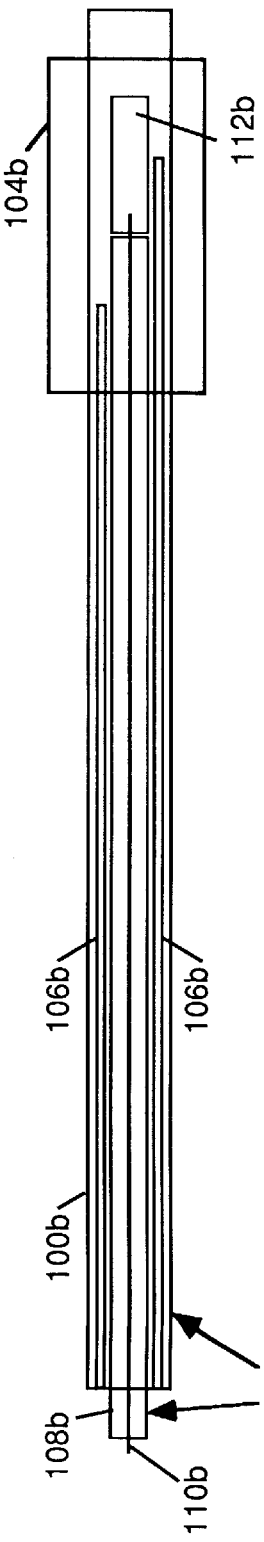

As schematically shown in FIG. 1b, the urethral ballon catheter of the present invention constitutes a single integrated structural unit comprising a first tubular balloon-supporting structure having a given outer diameter and a second structure inserted therein.

As indicated in FIG. 1b, the first and second substructures of the integrated-structure urethral balloon catheter of the present invention are physically attached to one another. More specifically, elements 10b, 104b, 106b, 108b, 110b and 112b of FIG. 1b functionally correspond, respectively, to above-described elements 100a, 104a, 106a, 108a, 110a and 112a of FIG. 1a. However, because the first and second substructures of the integrated-structure urethral balloon catheter of FIG. 1b are physically attached to one another, no centrally-located lumen, as such, corresponding to centrally-located lumen 102a is required in FIG. 1b, since centrally-located coaxial cable 108b with its attached microwave antenna 112b needs no clearance for their insertion. Thus, the outer diameter of coaxial cable 108b and the width of microwave antenna 112b is increased in size to the size occupied in FIG. 1a by the entire diameter of centrally-located lumen 102a. Therefore, by comparing the integrated-structure urethral balloon catheter schematically shown in FIG. 1b with the prior-art urethral balloon catheter structure schematically shown in FIG. 1a, it can be seen that the diameter of coaxial cable 108b and the width of microwave antenna 112b are significantly larger than the diameter of coaxial cable 108a and the width of microwave antenna 112a. This desirably decreases the microwave power loss in coaxial cable 108b with respect to that in coaxial cable 108a and increases the radiating efficiency of microwave antenna 112b with respect with respect to that of microwave antenna 112a.

Figure 2:
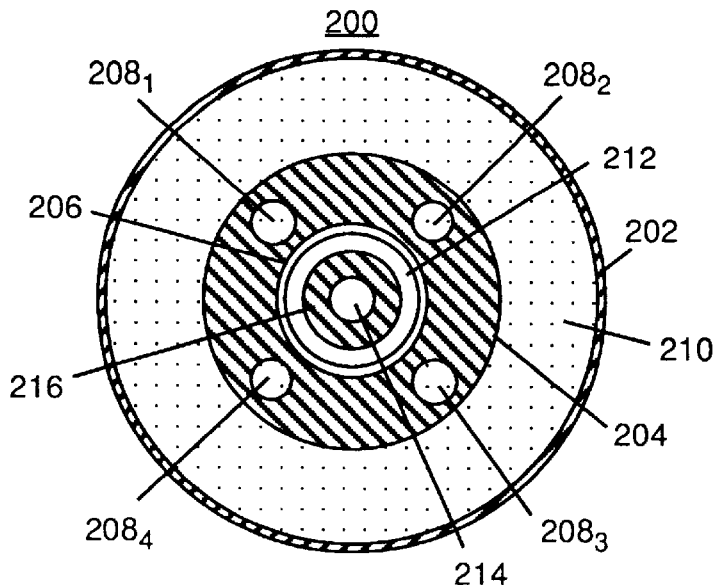
FIG. 2 is a detailed cross-sectional view of a representative structure of a prior-art urethral balloon catheter incorporating a microwave antenna.

Referring now to FIG. 2, there is shown a cross-sectional view of a representative structure 200 of a prior-art urethral balloon catheter incorporating a microwave antenna (not shown), with the balloon 202 thereof being fully inflated. The first sub-structure comprises thick-walled tubular plastic catheter structure 204 having an outer diameter, which is sufficiently small (typically about 8 mm) to fit balloon 202 in its deflated folded state into the urethra of a male patient suffering from prostate disease, and an inner diameter defining centrally-located lumen 206. The wall of catheter structure 204 has four separate lumens $208_1$–$208_4$ therethrough. Balloon 202, which is attached to catheter structure 204, is composed of a pliable sheet of a plastic material similar to that employed for inflatable toys. Such pliable plastic sheet balloon material does not stretch significantly under the pressure of fluid 210 (indicated by stippling) sufficient to fully inflate balloon 202 while balloon 202 is squeezing the urethral tissue of a patient undergoing treatment for prostate disease. The second sub-structure, shown inserted within centrally-located lumen 206, comprises a coaxial cable composed of outer conductor 212 and inner conductor 214 separated from one another other by dielectric 216. The second sub-structure further includes a microwave antenna (not shown) attached to the distal end of the coaxial cable. As shown in FIG. 2, the diameter of outer conductor 212 is slightly smaller than the diameter of centrally-located lumen 206 to provide the required clearance for the insertion of the second sub-structure into centrally-located lumen 206. This limits the ratio of the unexpanded catheter diameter (8.0 mm) to the antenna/cable diameter (2.2 mm) to substantially 3.6:1.

Balloon 202 is fully inflated by continuously circulating fluid 210 under back pressure which enters the interior of balloon 202 through certain one or more of separate lumens $208_1$–$208_4$ and exits the interior of balloon 202 through another one or more of separate lumens $208_1$–$208_4$. The circulating fluid may also serve the purpose of cooling the heated urethral tissue located proximate to the catheter of a patient undergoing treatment.

Figure 3:
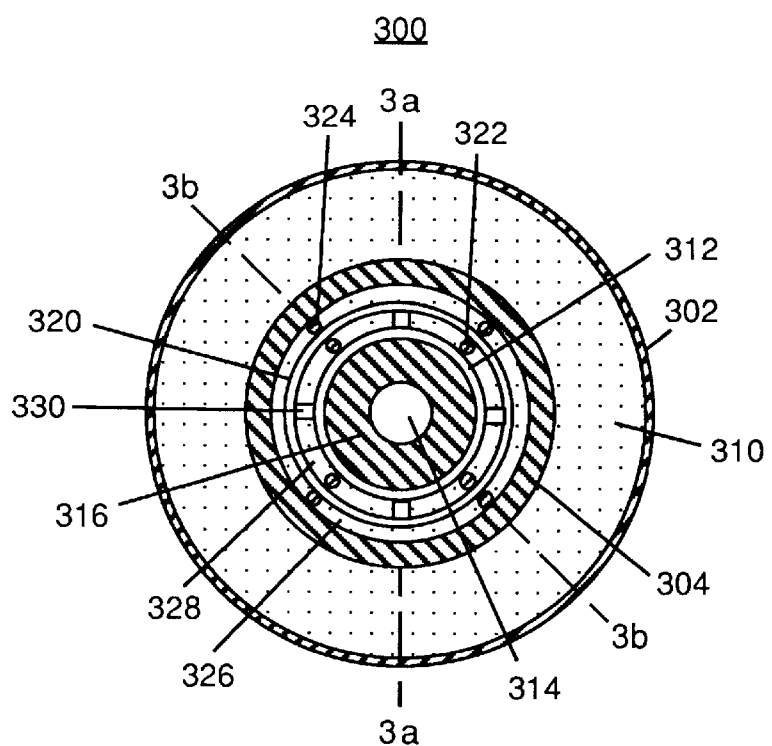
FIG. 3 is a detailed cross-sectional view of a basic embodiment of a urethral balloon catheter incorporating a microwave antenna structure in accordance with the principles of the present invention.
Figure 3A:
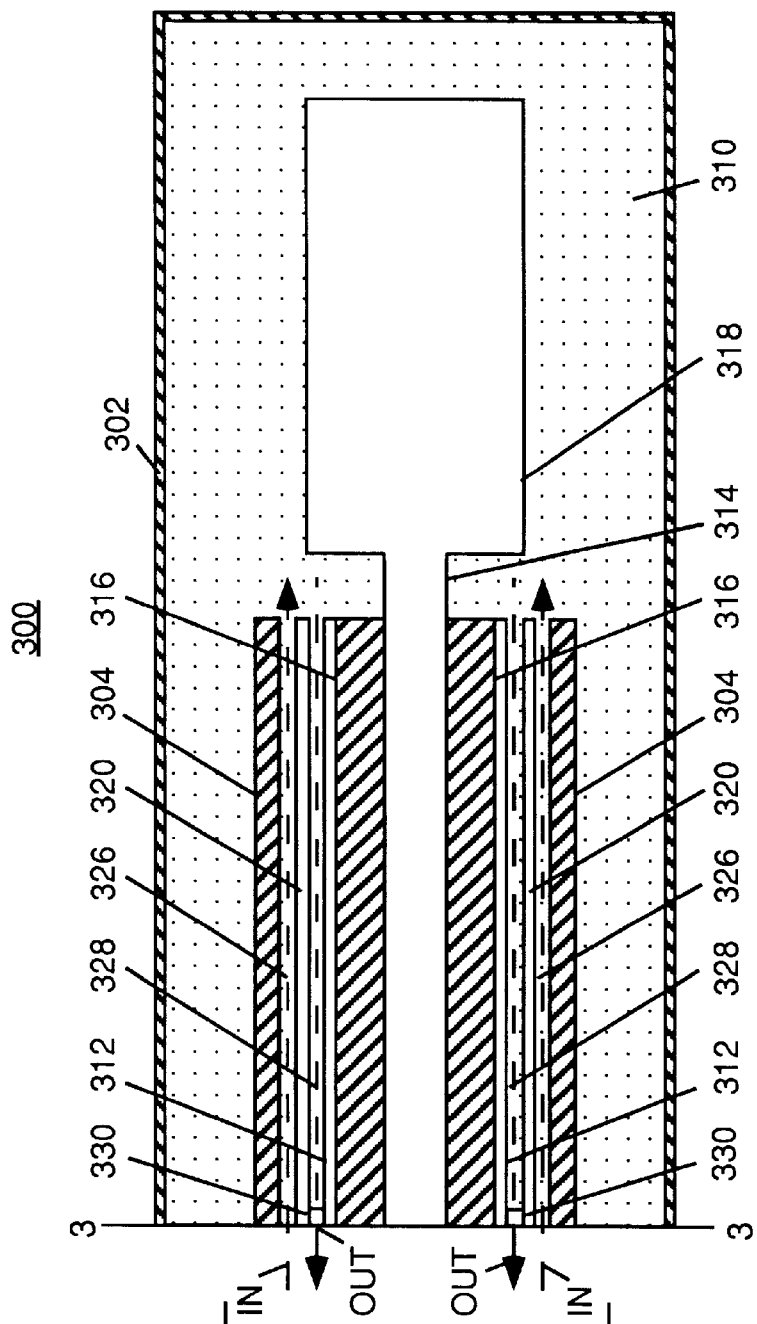
FIG. 3a is a detailed side view of the structure of FIG. 3 through the longitudinal plane designated by dashed line 3a, FIG. 3b is a detailed side view of the structure of FIG. 3 through the longitudinal plane designated by dashed line 3b.
Figure 3B:
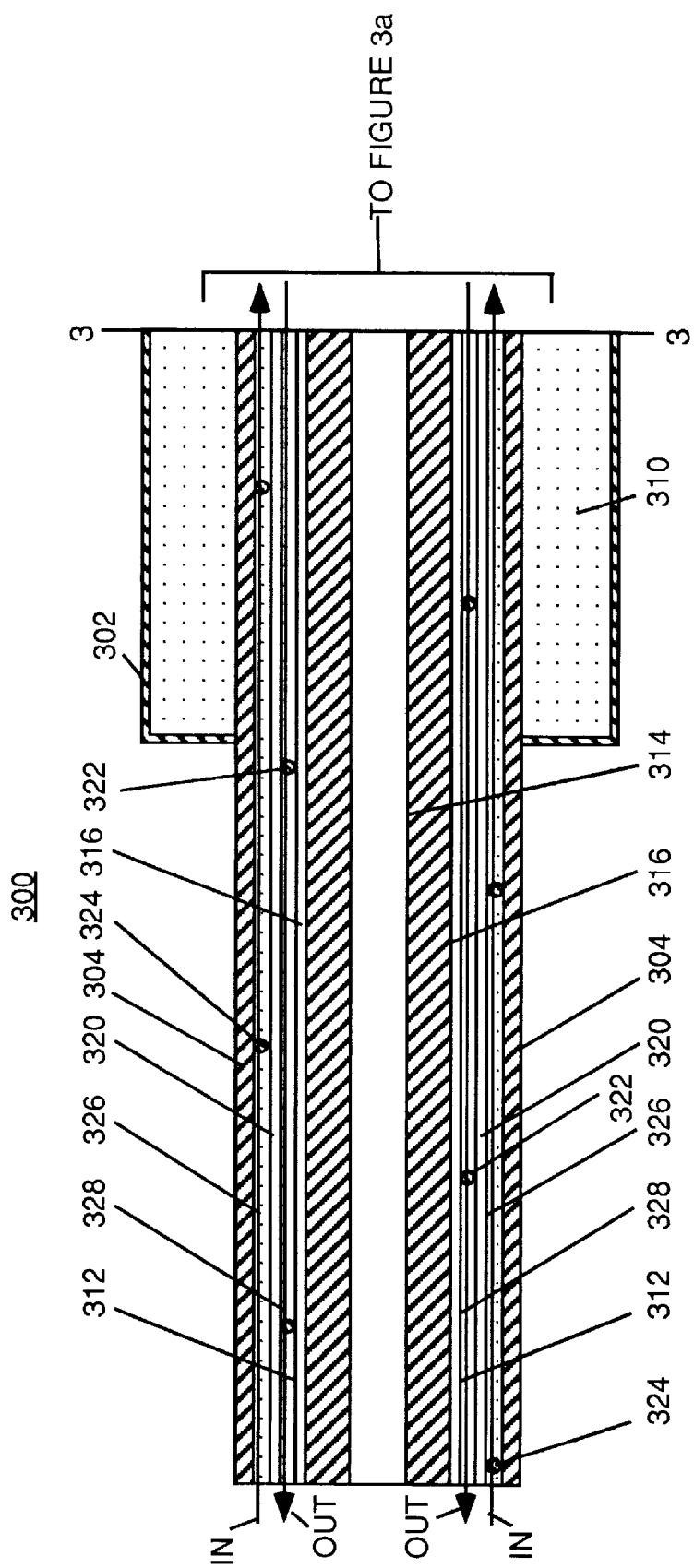

Referring now to FIGS. 3, 3a and 3b, which, respectively, show a cross-sectional view and first and second longitudinal views (indicated by dashed-lines 3a—3a and 3b—3b of the FIG. 3 cross-sectional view structure, with the first longitudinal view of FIG. 3a showing a distal portion of integrated structure 300 situated to the right of the cross-sectional view of FIG. 3 and the second longitudinal view of FIG. 3b showing a proximate portion of integrated structure 300 situated to the left of the cross-sectional view of FIG. 3) of a basic embodiment of a urethral balloon catheter incorporating a microwave antenna in accordance with the principles of the present invention, with the balloon 302 thereof being fully inflated. Balloon 302, which is attached to catheter structure 304, is composed of a pliable sheet of a plastic material similar to that employed for inflatable toys. Such pliable plastic sheet balloon material does not stretch significantly under the pressure of fluid 310 (indicated by stippling) sufficient to fully inflate balloon 302 while balloon 302 is squeezing the urethral tissue of a patient undergoing treatment for prostate disease. Integrated structure 300 comprises a tubular plastic catheter structure 304 having an outer diameter, similar in size (8 mm) to the outer diameter of above-described catheter structure 204, which is sufficiently small to fit balloon 302 in its deflated folded state into the urethra of a male patient suffering from prostate disease. However, the inner diameter of catheter structure 304 is considerably larger than the inner diameter of above-described catheter structure 204 that defines centrally-located lumen 206. This provides room for both (1) a centrally-located coaxial cable consisting of an outer conductor 312, inner conductor 314 and dielectric 316, that have diameters which are substantially larger than the diameters of an outer conductor 212, inner conductor 214 and dielectric 216, (2) a microwave antenna 318 (shown in FIG. 3a) which is substantially wider than is a microwave antenna that is capable of fitting into lumen 206, and (3) a tubular metallic shield 320 having a cross section located in spaced relationship with both outer conductor 312 of the coaxial cable and the inner diameter of catheter structure 304, as shown in FIG. 3.

As shown in FIGS. 3 and 3b, metallic shield 320 of integrated catheter structure 300 is physically maintained in its spaced relationship by a first set of springy plastic spacers 322 situated between coaxial-cable outer conductor 312 and metallic shield 320 and by a second set of springy plastic spacers 324 situated between metallic shield 320 and the inside surface of tubular catheter structure 304. As indicated in FIGS. 3 and 3b, the individual spacers of each of the first and second sets are longitudinally and angularly displaced from one another. This provides first annular channel 326 between metallic shield 320 and the inside surface of tubular catheter structure 304 for continuously circulating fluid 310 under back pressure to enter the interior of balloon 302 and second annular channel 328 between metallic shield 320 and coaxial-cable outer conductor 312 for the continuously circulating fluid 310 under back pressure to exit the interior of balloon 302.

As known, any antenna with a limited size ground plane (the situation in this case) causes a significant amount of reflected microwave energy to flow back from the distal end of the coaxial cable along the outer conductor thereof. However, a ¼ wavelength choke may be employed to considerably reduce the amount of this flowed-back reflected microwave energy. Therefore, as shown in FIGS. 3 and 3a, the present invention employs metal spacers 330 to provide a built-in ¼ wavelength choke. More specifically, the built-in ¼ wavelength choke is formed by providing an open-circuit impedance at the distal end of the coaxial cable and employing metal spacers 330 to short-circuit metallic shield 320 to coaxial-cable outer conductor 312 at a certain distance from the distal end of the coaxial cable which is equal to ¼ wavelength of reflected microwave-energy signal traveling back from the distal end of the coaxial cable through fluid 310 (e.g., low-loss deionized water). The built-in ¼ wavelength choke reduces the undesirable flow of this reflected microwave-energy signal. Further, because the dielectric constant of deionized water, which is close to that of muscle tissue, is approximately 75 (a factor in the order of 8.7 larger than that of a coaxial choke using a conventional dielectric), the built-in ¼ wavelength choke of FIGS. 3 and 3a is almost four times shorter in length than a coaxial choke using a conventional dielectric. As indicated in FIG. 3, metal spacers 330 are angularly displaced from the springy plastic spacers 322 and 324 of both the first and second sets. Therefore, although not shown in the FIG. 3a, the distal portion of integrated structure 300 may also include springy plastic spacers 322 and 324 having locations which are angularly spaced from metal spacers 330.

As shown in FIGS. 3a and 3b, the presence of metallic shield 320 results in an a spatial antenna radiation pattern from antenna 318 that provides a limited region of the patient's tissue where the radiated microwave is to applied and, therefore, a sharply-defined heating zone of this tissue. Thus, the presence of shield 320 protects critical tissue of the patient from damage during treatment. For example, the external sphincter would be protected from being heated by the presence of shield 320, thereby lessening the chance of damage leading to permanent incontinence.

Figure 4:
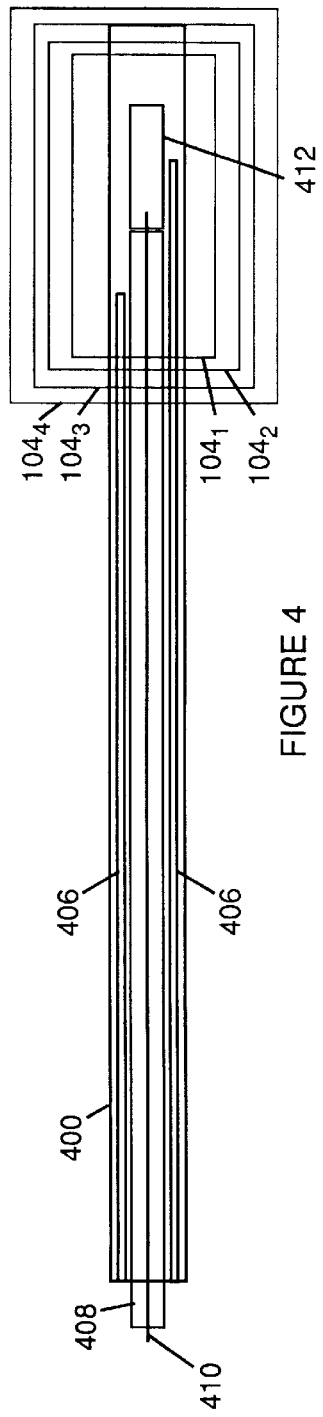
FIG. 4 shows a modification of the primary structure of the urethral balloon catheter shown in FIG. 1b which employs a plurality of balloons that have different fully-inflated sizes and FIG. 4a is a detailed cross-sectional view of an embodiment of such a plural-balloon urethral balloon catheter that, in most respects, is similar in structure to the structure of the basic embodiment shown in FIG. 3.
Figure 4A:
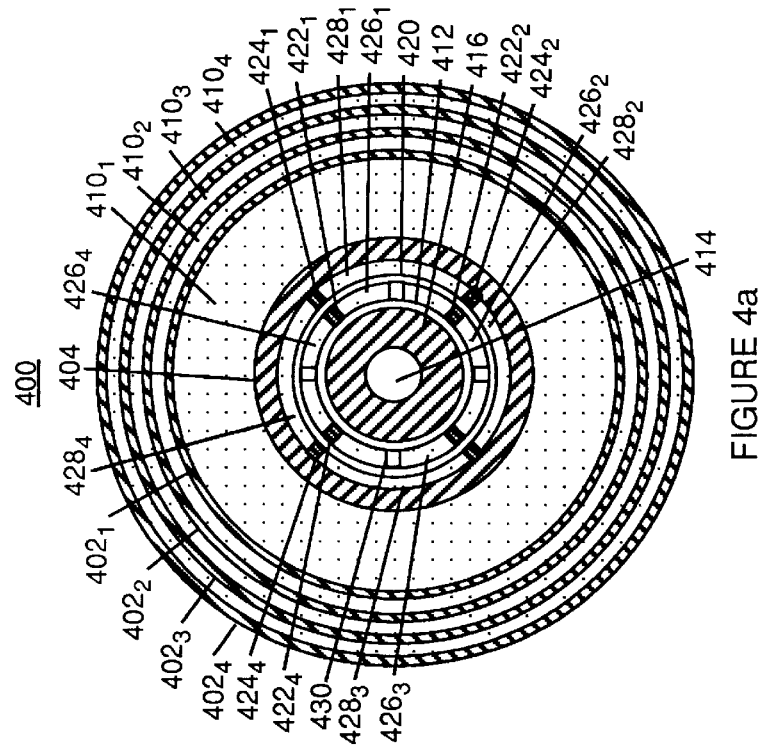

The above-described basic embodiment of the present invention shown in FIGS. 3, 3a and 3b, which employs springy plastic spacers 322 and 324 for maintaining shield 320 in spaced relationship with outer conductor 312 of the coaxial cable and the inner surface of plastic catheter structure 304, defines only a single input annular channel 326 and a single output annular channel 328 for the continuously circulating fluid 310. However, there are cases wherein it is desired to have a plurality of separated input and output channels for independently circulating fluid to more than a single inflatable balloon. One of such cases, known in the art and taught in the aforesaid Sterzer patent, is the use of a Foley balloon placed in the patient's bladder to anchor the catheter's position within the patient's urethra. Another case, shown in FIGS. 4 and 4a, is the use of a plurality of independently-inflatable nested balloons which increase in fully-inflated size (shown in FIG. 4a) from the smallest innermost balloon to the largest outermost balloon. In all such cases, the springy plastic spacers 322 and 324 of FIGS. 3, 3a and 3b may be replaced by plastic separator ribs that extend longitudinally the entire length the catheter structure to thereby define a plurality of angularly-separated input and output channels.

More specifically, the integrated-structure urethral balloon catheter 400 schematically shown in FIGS. 4 and 4a comprises 4 nested inflatable balloons $404_1$, $404_2$, $404_3$ and $404_4$, rather than comprising the single inflatable balloon 104b of the integrated-structure urethral balloon catheter schematically shown in FIG. 1b. As shown in FIG. 4a, the 4 plastic separator ribs $424_1$, $424_2$, $424_3$ and $424_4$ situated between metallic shield 420 and the inside surface of tubular catheter structure 404 provides 4 angularly-separated channel sectors $426_1$, $426_2$, $426_3$ and $426_4$, of approximately 90° each for input circulating fluid $410_1$, $410_2$, $410_3$ and $410_4$, to independently enter the interior of each of balloons $404_1$, $404_2$, $404_3$ and $404_4$, while the 4 plastic separator ribs $422_1$, $422_2$, $422_2$ and $422_4$ situated between coaxial-cable outer conductor 412 and metallic shield 420 provides 4 angularly-separated channel sectors $428_1$, $428_2$, $428_3$ and $428_4$ of approximately 90° each for output circulating fluid $410_1$, $410_2$, $410_3$ and $410_4$, to independently exit the interior of each of balloons $404_1$, $404_2$, $404_3$ and $404_4$. In other respects, integrated-structure urethral balloon catheter 400 corresponds structurally and functionally to the above-described integrated-structure urethral balloon catheter 300.

The purpose of nested balloons $404_1$, $404_2$, $404_3$ and $404_4$ is to provide a choice of fully-inflated size during the treatment without withdrawal of the catheter and replacement with a new catheter of a different size. Typically, the innermost balloon $404_1$ would be fully-inflated first. If the patient tolerated this procedure and the fully-inflated pressure was within determined limits, both indicating that a greater fully-inflated size would be both feasible and desirable, the balloon $404_2$ would be fully-inflated. Similarly, the $404_3$ and $404_4$, balloons would be fully-inflated if the patient could tolerate a greater degree of prostate expansion and all safety considerations were satisfied.

The number of nested balloons is not limited to 4 balloons, as shown in FIGS. 4 and 4a, but could be smaller or larger, with each of the angularly-separated input and output channel sectors being larger or smaller than 90°.

Further, at the end of the treatment and a short relaxing time for the patient, but before withdrawal of the catheter applicator, the nested balloons could be expanded slowly, one after another, while the back pressure is being monitored. A discontinuous increase in back pressure will indicate that the prostate is resisting expansion. Knowing the size of the balloon in use when this occurs will provide a measure of the new size of the treated prostate. In this regard, reference is made to the teachings of allowed U.S. patent application Ser. No. 99/137,230, filed Aug. 20, 1998, which teachings are incorporated herein by such reference.

The above-described basic embodiment of the urethral balloon catheter of the present invention, shown in FIGS. 3, 3a and 3b, which incorporates a minimum number of structural changes with respect to the above-described representative prior-art urethral balloon catheter, shown in FIG. 2, is effective in increasing the ratio of the unexpanded unchanged catheter diameter (8.0 mm) to the physically-attached antenna/cable diameter to more than 3.6:1 by doing away for the need for clearance. However, the preferred embodiment of the urethral balloon catheter of the present invention, shown in FIGS. 5 and 5a described below which incorporates a large number of structural changes with respect to both the above-described representative prior-art and basic embodiments of the urethral balloon is effective in decreasing the unexpanded catheter diameter to substantially 6.0 mm while further increasing the antenna/cable diameter to substantially 4.0 mm, whereby the ratio of the unexpanded catheter diameter to the antenna/cable diameter is significantly increased to about 1.5.

Figure 5:
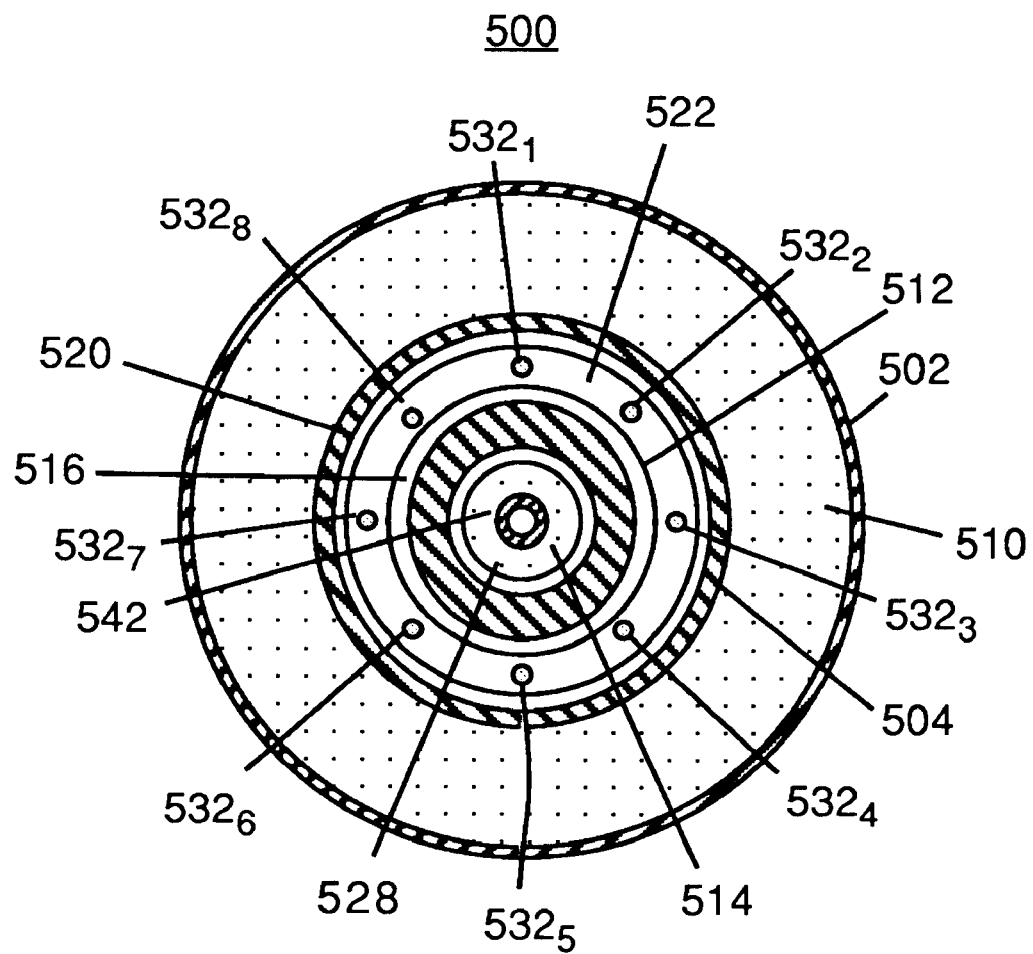
FIG. 5 is a detailed cross-sectional view of a preferred embodiment of a urethral balloon catheter incorporating a microwave antenna structure in accordance with the principles of the present invention and FIG. 5a is a detailed side view of the structure of FIG. 3.
Figure 5A:
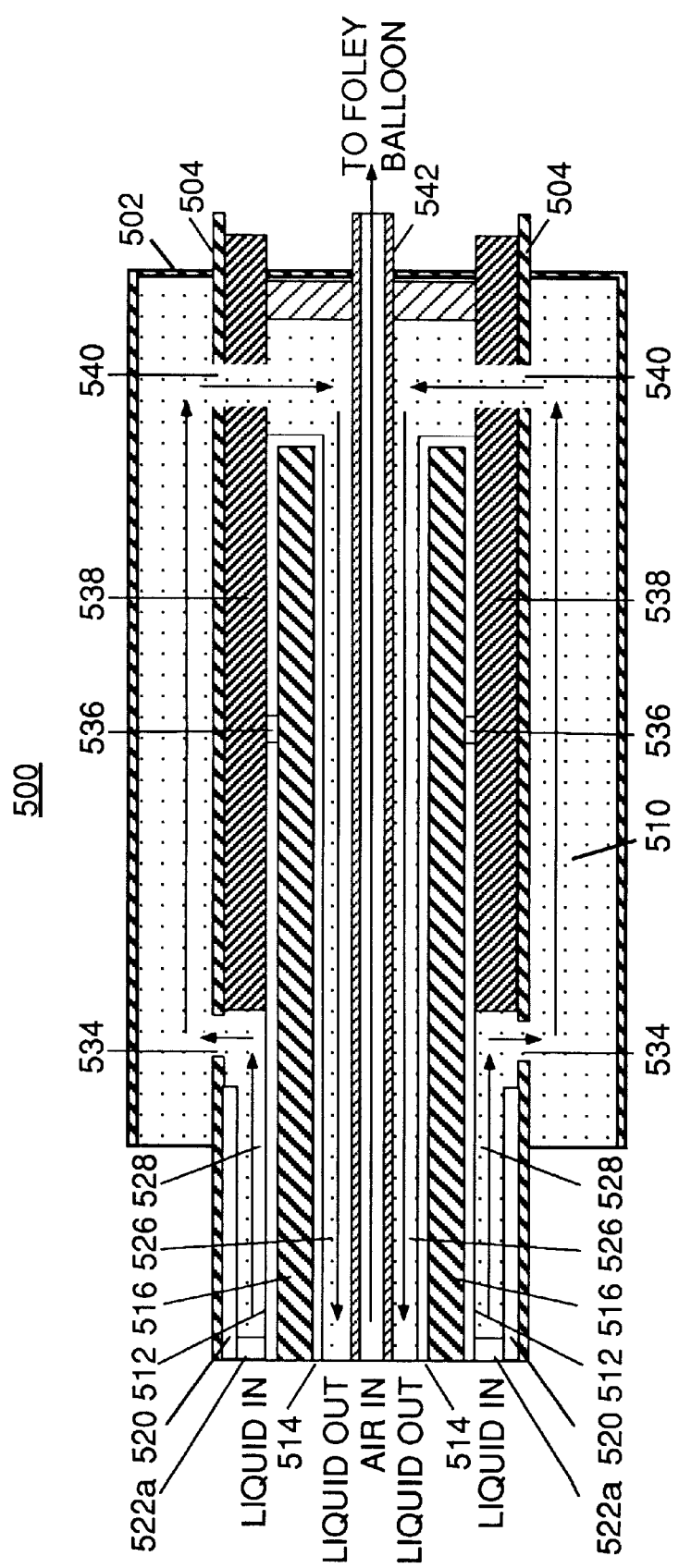

Specifically, in the integrated structure 500 of the preferred embodiment of the urethral catheter shown in FIGS. 5 and 5a, the diameter of fully-inflated balloon 502 and the outer diameter of tubular plastic catheter structure 504 may be the same as the diameter of fully-inflated balloon 302 and the outer diameter of tubular plastic catheter structure 304. However, tubular metallic shield 520 is contiguous with the inner surface of plastic catheter structure 504. Preferably, shield 520 comprises a thin metal foil bonded to the inner surface of plastic catheter structure 504. At least one ring 522, situated between coaxial-cable outer conductor 512 and shield 520 provides physical support for them, so that plastic catheter structure 504 may be less thick than plastic catheter structure 304. Ring 522a, shown in FIG. 5a, is a metal ring that comprises a ¼ wavelength choke situated near the distal end of the coaxial cable by short-circuiting shield 520 to conductor 512. Additional ones of longitudinally-spaced rings 522 (not shown) comprising plastic may be employed for supporting the unshown proximate portion, if any, of plastic catheter structure 504 that would be situated, in FIG. 5a, to the left of metal ring 522a. A set of 8 spaced holes $532_1$ to $532_8$ through each of rings 522 permit balloon-inflating liquid 510 (preferably deionized water) flowing through input channel 526 to pass rings 522 and enter balloon 502 through a plurality of angularly spaced holes 534 distributed about the circumference of plastic catheter structure 504.

The coaxial cable of the preferred embodiment comprises outer conductor 512 separated from thin-walled tubular inner conductor 514 by dielectric 516. The distal ends of outer and inner conductors 512 and 514 are short-circuited and a gap antenna is formed by gap 536 situated about ¼ wavelength from the distal end of outer conductor 512. A high-dielectric insulator 538 (e.g., titania) extends from at least ¼ wavelength to the left of gap 536 to a point well beyond the distal end of the coaxial cable.

The hollow interior of inner conductor 514 is employed as output channel 526 for balloon-inflating liquid 510 exiting balloon 502 through a plurality of angularly spaced holes 540 distributed about the circumferences of dielectric insulator 538 and plastic catheter structure 504 that are longitudinally situated slightly to the right of the distal end of the coaxial cable, as shown in FIG. 6a. The interior of inner conductor 514 carries little of the microwave signal (high frequencies travel along its outside surface) but it is the point of heat concentration produced by cable losses. Therefore, balloon-inflating liquid 510 (preferably deionized water) flowing through output channel 526 defined by the interior of inner conductor 514 will have minimal effect on the microwave power but maximum effect on carrying away cable dissipation heat without adding significantly to the diameter of the overall structure. Further, the hollow interior of inner conductor 514 may house either a permanent or removable thin tube 542 used to forward air to inflate a Foley balloon (not shown). If removable, such a Foley balloon would incorporate a self-closing "flap" known type valve, in which re-insertion would force open the seal and permit deflation.

Because the antenna of the integrated structure of the aforesaid embodiments of the urethral catheters employing a microwave antenna of the present invention is fixed in position relative to the catheter structure, each assembly thereof may be pre-tuned so that it is optimally matched to muscle tissue thereby reducing mismatch loss and cable heating. Further, the integrated structure of the aforesaid embodiments of the present invention permits many desirable modifications not available to prior-art non-integrated structures of urethral catheters employing a microwave antenna. For instance, shielding 320, 420 or 520 could be modified to obtain a directional radiation of microwave or RF energy for some special purpose such as preferential treatment of one side of the prostate. In addition, an important feature of shielding 320, 420 or 520 is that it will makes it practical to use the microwave antenna as the pickup for a radiometer to measure prostate temperature. With a prior-art unshielded antenna coaxial cable disposed inside the catheter, radio signals in the vicinity will interfere with the radiometer which must be able to detect extremely low level signals to measure temperature by radiometric techniques.

Because of the nature of the application, it is impractical to shield the prior-art catheter because the outer conductor cannot be contacted properly because it is covered by the plastic catheter sheath.

Also, since in the microwave balloon treatment, it is important to know that the balloon has been fully expanded, the integrated-structure catheter could include mechanical or electrical means to determine the degree of inflation. Separate input and output channels could be provided for pressure measurements of each of the one or more inflation balloons from which flow vs. pressure measurements would show when full inflation had occurred, as taught in the aforesaid allowed U.S. patent application Ser. No. 09/137,230. Small spring (plastic) actuated parts could be incorporated that would "unfurl" only when full expansion had occurred. The coaxial cable could be used as a probe by inputting a very low level signal at some frequency and sensing a flange caused by the spring action —or possibly by the balloon motion cessation—by monitoring the reflected signal at that frequency.

One other feature which can be added as a part of an integrated catheter assembly is the inclusion of RF or microwave circuitry within the catheter itself. This circuitry could consist of active or passive components for various purposes.

For a first example, in an integrated catheter assembly there would be sufficient room within the tubular catheter structure to include an antenna suitable for radiometer use together with incorporated distal end circuitry proximate to the antenna comprising a low-noise amplifier and, where applicable, related passive circuits such as a directional coupler. This would have the advantage of stabilizing the input noise figure so that the cable loss would not degrade the noise figure as is the case if the low noise amplifier is after the coaxial cable. In the catheter application, the coaxial cable diameter is necessarily small and consequentially has high loss. Putting the amplifier at the antenna before the coaxial cable improves the radiometer performance by moving the coaxial cable loss on the output side of the low-noise amplifier. Another benefit is that the sensitivity to external pickup will be reduced. The part of the catheter and coaxial cable that is outside the patient is subject to picking up extraneous radio noise and interference. Since the radiometer functions with a very low level of signal, this pickup can seriously degrade accuracy and stability. If the signal is preamplified before the catheter exits the patient, the effect of pickup will be lessened because it will be a smaller part of the overall signal applied to the remaining radiometer circuit.

Further, by incorporating an output amplifier stage inside the catheter proximate to the antenna for increasing the power of the microwave energy radiated therefrom, only a relatively low power signal need be sent through the small coaxial feedline cable. This (1) reduces the absolute power loss in the coaxial cable which, in turn, reduces the effective thermal radiation of power from the coaxial cable into the targeted tissue, as well as eliminating cable heating, all of which complicate thermal management.

Other features that could be built into integrated catheters for various specialized functions include optical fibers, microphone pickups, temperature sensors, pressure sensors, and electronic tuners to optimize antenna match.

Integrated catheters employing one or more features of the present invention are not limited to only integrated urethral catheters. The same basic integrated antenna-catheter construction could be used in other body pipes, such as rectum, colon, esophagus or arteries (e.g., angioplasty) for opening narrowed passages or treating malignancies.

Further, there are situations where it is desirable to provide a system that incorporates a pair of integrated antenna-catheters that cooperate in providing therapeutic treatment of a disease. For instance a diseased prostate situated between the urethra and rectum could be treated more effectively by employing both a first integrated antenna-catheter situated in the urethra and a second integrated antenna-catheter situated in the rectum. Preferably, the antennas should have a directional design in order to concentrate the microwave power on the diseased prostate. Such a system could employ an RF switch controller for transmitting microwave power from a microwave power source alternately from the antenna of the first integrated antenna-catheter and from the antenna of the second integrated antenna-catheter, while simultaneously forwarding microwave power received by the antenna of the then non-transmitting one of the first and second integrated antenna-catheters to a microwave receiver for monitoring the microwave power going through the prostate to detect changes during the process.

What is claimed is:

1. In a urethral balloon catheter incorporating an antenna suitable for use in therapeutically heating a diseased prostate of a male patient with energy radiated from said antenna, wherein said urethral catheter comprises (1) a tubular catheter first structure longitudinally extending from a proximate end thereof to a distal end thereof that includes an attached inflatable balloon situated near the distal end thereof together with input and output channels for use in circulating a balloon-inflating fluid, said tubular catheter first structure having a given outer diameter sufficiently small to permit it to be inserted inside of the urethra of said male patient with said balloon in its deflated state, and (2) a second structure inserted within said tubular catheter first structure that comprises said antenna situated toward said distal end of said tubular catheter first structure and a longitudinal coaxial cable comprising an inner conductor having a first given diameter, an outer conductor having a second given diameter and a dielectric having a given dielectric constant situated between said inner and outer conductors, said coaxial cable extending from the proximate end of said tubular catheter first structure to said antenna for use in energizing said antenna; the improvement wherein:

said tubular catheter first structure and said second structure of said urethral balloon catheter are constructed to comprise a single integrated structural unit that includes interface structure comprising a longitudinal electrically conductive shield physically attached to both said outer conductor and an inner surface of said tubular catheter first structure;

whereby both said antenna and said longitudinal cable may be wider, without any increase in said given outer diameter, than would be the case if said urethral balloon catheter were a non-integrated structure in which said tubular catheter first structure and said second structure constitute separate units that are detached from one another and, therefore, would require clearance between the second structure and the tubular catheter first structure sufficient for a non-permanent insertion of the second structure within the tubular catheter first structure.

2. The urethral balloon catheter defined in claim 1, wherein said interface structure further comprises:

a first set of spacing means positioned to maintain said shield in spaced relationship with respect to said outer conductor of said coaxial cable and form at least one inner channel therebetween; and a second set of spacing means positioned to maintain said shield in spaced relationship with respect to said inner surface of said tubular catheter first structure and form at least one outer channel therebetween;

whereby an inner channel may be selectively employed as a certain one of either said input channels or, alternatively, said output channels for use in circulating said balloon-inflating fluid, while an outer channel then is employed as the remaining one of either said output channels or, alternatively, said input channels for use in circulating said balloon-inflating fluid.

3. The urethral balloon catheter defined in claim 2, wherein:

said inner channel is employed as an output channel for use in circulating said balloon-inflating fluid and said outer channel is employed as an input channel for use in circulating said balloon-inflating fluid.

4. The urethral balloon catheter defined in claim 2, wherein:

said electrically conductive shield comprises a metal shield;

said first set of spacing means comprises longitudinally and circumferentially distributed springy plastic spacers situated between said metal shield and said outer conductor of said coaxial cable to form a single inner channel therebetween; and said second set of spacing means comprises longitudinally and circumferentially distributed springy plastic spacers situated between said metal shield and said inner surface of said tubular catheter first structure to form a single outer channel therebetween.

5. The urethral balloon catheter defined in claim 2, wherein:

said electrically conductive shield comprises a metal shield;

said first set of spacing means comprises a given plural number of circumferentially-distributed longitudinal plastic ribs situated between said metal shield and said outer conductor of said coaxial cable which are angularly spaced in position to form a number of separate inner channels therebetween equal in number to said given number; and said second set of spacing means comprises said given plural number of circumferentially-distributed longitudinal plastic ribs situated between said metal shield and said inner surface of said tubular catheter first structure which are angularly spaced in position to form a number of separate outer channels therebetween equal in number to said given number.

6. The urethral balloon catheter defined in claim 5, wherein:

said tubular catheter first structure comprises attached different-size inflatable balloons equal in number to said given plural number that individually correspond to a different pair of inner and outer channels of said given plural number of separate inner and outer channels;

whereby each separate one of said given plural number of inflatable balloons is independently inflatable by circulating a balloon-inflating fluid through that pair of inner and outer channels with which that inflatable balloon corresponds.

7. The urethral balloon catheter defined in claim 2, wherein:

said circulating balloon-inflating fluid comprises a given liquid exhibiting a predetermined dielectric constant that flows in said outer channel;

said antenna attached to the distal end of said coaxial cable is energized through said coaxial cable by energy of a given wavelength to be radiated by said antenna;

the distal end of said coaxial cable is open-circuited; and said interface structure further comprises electrically conductive means for short-circuiting said electrically conductive shield to said outer conductor of said coaxial cable at a certain distance from the distal end of said coaxial cable, which certain distance has a value, as a function of the value of said predetermined dielectric constant of said given liquid, which substantially provides a ¼ wavelength choke at said given wavelength;

whereby the presence of said ¼ wavelength choke considerably reduces the backward flow of reflected given-wavelength energy.

8. The urethral balloon catheter defined in claim 7, wherein:

said a given liquid is deionized water having a predetermined dielectric constant of approximately 75 in value.

9. The urethral balloon catheter defined in claim 1, wherein:

said shield is contiguous with said inner surface of said tubular catheter first structure;

said interface structure further comprising a set of spacing means positioned to maintain said shield in spaced relationship with respect to said outer conductor of said coaxial cable and form at least one outer channel therebetween; and said inner conductor comprises a tubular inner conductor having an interior that forms at least one inner channel;

whereby an inner channel may be selectively employed as a certain one of either said input channels or, alternatively, said output channels for use in circulating said balloon-inflating fluid, while an outer channel then is employed as the remaining one of either said output channels or, alternatively, said input channels for use in circulating said balloon-inflating fluid.

10. The urethral balloon catheter defined in claim 9, wherein:

each of said set of spacing means comprises a solid ring that includes a plurality of holes through which said circulating balloon-inflating fluid can flow.

11. The urethral balloon catheter defined in claim 9, wherein:

said inner channel is employed as an output channel for use in circulating said balloon-inflating fluid and said outer channel is employed as an input channel for use in circulating said balloon-inflating fluid.

12. The urethral balloon catheter defined in claim 9, wherein:

said circulating balloon-inflating fluid comprises a given liquid exhibiting a predetermined dielectric constant that flows in said outer channel;

said antenna attached to the distal end of said coaxial cable is a gap antenna that is energized through said distal end of said coaxial cable by energy of a given wavelength to be radiated by said antenna; wherein said gap antenna is formed by a gap in said outer conductor that effectively open-circuits said distal end of said coaxial cable; and said interface structure further comprises electrically conductive means for short-circuiting said electrically conductive shield to said outer conductor of said coaxial cable at a certain distance from the distal end of said coaxial cable, which certain distance has a value, as a function of the value of said predetermined dielectric constant of said given liquid, which substantially provides a ¼ wavelength choke at said given wavelength;

whereby the presence of said ¼ wavelength choke considerably reduces the backward flow of reflected given-wavelength energy.

13. The urethral balloon catheter defined in claim 12, wherein:

said electrically conductive means for short-circuiting said electrically conductive shield to said outer conductor of said coaxial cable comprises a solid metal ring that includes a plurality of holes through which said circulating balloon-inflating fluid can flow.

14. The urethral balloon catheter defined in claim 12, further comprising:

a solid insulating material exhibiting a given dielectric constant situated between said gap antenna and said inner surface of said tubular catheter first structure.

15. The urethral balloon catheter defined in claim 14, wherein:

said given dielectric constant exhibited by said solid insulating material a given dielectric constant is in the vicinity of the dielectric constant of muscle tissue.

16. The urethral balloon catheter defined in claim 15, wherein:

said solid insulating material is titania.

17. The urethral balloon catheter defined in claim 12, wherein:

said a given liquid is deionized water having a predetermined dielectric constant of approximately 75 in value.

18. In a catheter incorporating an antenna, wherein said catheter comprises (1) a tubular catheter first structure longitudinally extending from a proximate end thereof to a distal end thereof and (2) a second structure inserted within said tubular catheter first structure that comprises said antenna situated toward said distal end of said tubular catheter first structure and a longitudinal coaxial cable comprising an inner conductor having a first given diameter, an outer conductor having a second given diameter and a dielectric having a given dielectric constant situated between said inner and outer conductors, said coaxial cable extending from the proximate end of said tubular catheter first structure to said antenna for use in energizing said antenna; the improvement wherein:

said tubular catheter first structure and said second structure of said catheter are constructed to comprise a single integrated structural unit that includes a longitudinal electrically conductive shield physically attached to both said outer conductor and an inner surface of said tubular catheter first structure.

* * * * *